(12) United States Patent
Lees (10) Patent No.: US 11,744,565 B2
(45) Date of Patent: Sep. 5, 2023

(54) SURGICAL EVACUATION APPARATUS AND METHOD

(71) Applicant: The Board of Regents of the University of Oklahoma, Norman, OK (US)

(72) Inventor: Jason Lees, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 380 days.

(21) Appl. No.: 16/754,656

(22) PCT Filed: Sep. 28, 2018

(86) PCT No.: PCT/US2018/053509
§ 371 (c)(1),
(2) Date: Apr. 8, 2020

(87) PCT Pub. No.: WO2019/074700
PCT Pub. Date: Apr. 18, 2019

(65) Prior Publication Data
US 2020/0352553 A1    Nov. 12, 2020

Related U.S. Application Data

(60) Provisional application No. 62/569,772, filed on Oct. 9, 2017.

(51) Int. Cl.
| | |
|---|---|
| *A61B 17/00* | (2006.01) |
| *A61B 17/3203* | (2006.01) |
| *A61B 17/32* | (2006.01) |

(52) U.S. Cl.
CPC .... *A61B 17/00234* (2013.01); *A61B 17/3203* (2013.01); *A61B 2017/00561* (2013.01);
(Continued)

(58) Field of Classification Search
CPC ...................... A61B 17/00234; A61B 17/3203
See application file for complete search history.

(56) References Cited

U.S. PATENT DOCUMENTS 1,114,268 A  * 10/1914  Kells ........................ A61M 1/28
                                                                          604/290
5,248,297 A     9/1993  Takase
(Continued)

OTHER PUBLICATIONS

International Search Report and Written Opinion (PCT/US/2018/053509) dated Dec. 10, 2018.
(Continued)

*Primary Examiner* — Si Ming Ku
(74) *Attorney, Agent, or Firm* — Dunlap Codding, P.C.

(57) ABSTRACT

A surgical evacuation apparatus and method for evacuating a biological material from a body cavity. The surgical evacuation apparatus has a shaft and a scoop extending from a distal end of the shaft. The shaft has a supply inlet for connecting to a pressurized fluid source and an outlet for connecting to a vacuum source. An evacuation channel extends from the scoop to the outlet. A fluid supply channel extends in the shaft from the supply inlet towards the distal end and intersects the evacuation channel proximate the scoop. Material desired to be removed from the body cavity is collected in the scoop by a user. The biological material collected in the scoop is broken up by a fluid stream from the supply channel and is drawn into the evacuation channel by a vacuum applied by the vacuum source and is removed from the body cavity.

20 Claims, 6 Drawing Sheets

(52) U.S. Cl.
CPC ............. *A61B 2017/320064* (2013.01); *A61B 2217/005* (2013.01)

(56) References Cited

U.S. PATENT DOCUMENTS

| | | | |
|---|---|---|---|
| 5,496,267 A | | 3/1996 | Drasler et al. |
| 5,527,330 A | | 6/1996 | Tovey |
| 5,782,795 A | * | 7/1998 | Bays ................ A61B 17/32002 604/35 |
| 8,430,837 B2 | * | 4/2013 | Jenson .................... A61M 1/84 604/19 |
| 2004/0243157 A1 | * | 12/2004 | Connor .............. A61B 17/3203 606/159 |
| 2006/0100569 A1 | | 5/2006 | McRury et al. |
| 2008/0255596 A1 | | 10/2008 | Jenson et al. |
| 2013/0267891 A1 | * | 10/2013 | Malhi ............... A61B 17/32037 604/30 |
| 2015/0272780 A1 | | 10/2015 | Carriazo |
| 2015/0282821 A1 | | 10/2015 | Look et al. |
| 2015/0305764 A1 | | 10/2015 | Hoyte et al. |
| 2016/0015372 A1 | * | 1/2016 | Walak ................... A61B 10/04 600/567 |

OTHER PUBLICATIONS

Extended European Search Report (EP 18865796.9) dated Jun. 16, 2021, 7 pages.
European Office action (EP 18865796.9) dated Jan. 24, 2023; 3 pgs,.

* cited by examiner

SURGICAL EVACUATION APPARATUS AND METHOD

CROSS REFERENCE TO RELATED APPLICATIONS

This application is a U.S. National Stage Application under 35 U.S.C. § 371 of International Application No. PCT/US2018/53509, filed Sep. 28, 2018, which claims benefit under 35 U.S.C. § 119(e) to U.S. Ser. No. 62/569,772, filed Oct. 9, 2017, the entirety of each is hereby expressly incorporated by reference herein.

BACKGROUND

Minimally invasive surgery techniques have allowed medical professionals to access surgical sites via small incisions through the skin or through body orifices. Endoscopic, laparoscopic, and arthroscopic surgical procedures commonly employed include minimally invasive surgical techniques. Minimally invasive surgical procedures are often preferred to open surgical procedures for many applications because minimally invasive procedures induce less structural injury and inflammatory responses to patients during surgery and thus are associated with fewer potential complications and reduced recovery time.

Some minimally invasive techniques may involve the removal of damaged tissue or harmful viscous fluids. For example, such techniques may include thorascopic removal of hemothorax, thorascopic removal of empyema, and laparoscopic debridement of liver abscess or hepatic necrosis. Traditional methods for removing damaged tissue have required either open procedures or the utilization of multiple tools/instruments, such as endoscopic graspers, forceps, and various suction devices. To reduce the number of required tools, single-unit devices including ways for both irrigating and evacuating tissue have been developed. For example, some surgical procedures involve delivering a liquid jet directly to a tissue for cutting and ablating the tissue and evacuating the excised tissue through a suction channel coupled to an external vacuum source (for example, the VERSAJET™ system). However, delivering a liquid jet directly to the biological material can cause unintended damage to surrounding tissue, which is particularly undesirable for delicate surgical sites such as the lungs and liver. It is toward alleviating this and other disadvantages that the apparatus and method of the present disclosure are directed.

BRIEF DESCRIPTION OF THE DRAWINGS

FIG. 6 is a cross-sectional view of the distal end of the surgical evacuation apparatus illustrating material being broken up therein and evacuated there through.

DETAILED DESCRIPTION

The present disclosure is directed to a single-unit surgical evacuation apparatus, and method of use, that enables safe and easy collection and evacuation of deleterious materials such as non-viable tissues, debris, bacteria, and contaminants from an internal body cavity while preserving normal, viable tissues therein. The device directs a fluid (liquid) jet onto deleterious materials which have been captured in a scoop, causing maceration of the materials for removal via an evacuation channel. The device of the present disclosure is therefore unlike other surgical evacuation tools which apply a liquid jet directly upon viable tissue for debridement purposes. The harmful effects on normal tissues which result from such direct application of a liquid jet are therefore avoided.

Before further describing various embodiments of the present disclosure in more detail by way of exemplary description, examples, and results, it is to be understood that the embodiments of the present disclosure are not limited in application to the details as set forth in the following description. The embodiments of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. The embodiments of and application and use thereof can be made and executed without undue experimentation in light of the present disclosure. While the present disclosure has been described in terms of particular embodiments, it will be apparent to those of skill in the art that variations may be applied to the apparatus and/or methods and in the steps or in the sequence of steps of the methods described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the apparatus, methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the terms "at least one" or "plurality" will be understood to include one as well as any quantity more than one, including but not limited to, 2, 3, 4, 5, 6, 7, 8, 9, 10, 15, 20, 30, 40, 50, 100, or any integer inclusive therein, and/or any range described herein. The terms "at least one" or "plurality" may extend up to 100 or 1000 or more, depending on the term to which it is attached; in addition, the quantities of 100/1000 are not to be considered limiting, as higher limits may also produce satisfactory results. In addition, the use of the term "at least one of x, y and z" will be understood to include x alone, y alone, and z alone, as well as any combination of x, y and z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "a, b, c, or combinations thereof" is intended to include at least one of: a, b, c, ab, ac, bc, or abc, and if order is important in a particular context, also ba, ca, cb, cba, bca, acb, bac, or cab. Continuing with this example, expressly included are combinations that contain repeats of one or more item or term, such as bb, aaa, aab, bbc, aaabcccc, cbbaaa, cababb, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is-meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-30 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, as well as sub-ranges within the greater range, e.g., for 1-30, sub-ranges include but are not limited to 1-10, 2-15, 2-25, 3-30, 10-20, and 20-30. Reference to a range of 1-50 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, etc., up to and including 50. Reference to a series of ranges includes ranges which combine the values of the boundaries of different ranges within the series. Thus, to illustrate reference to a series of ranges, for example, a range of 1-1,000 includes, but is not limited to, 1-10, 2-15, 2-25, 3-30, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 3 mm to 25 cm therefore refers to and includes all values or ranges of values, and fractions of the values and integers within said range, including for example, but not limited to, 4 mm to 22.5 cm, 4 mm to 20 cm, 6 mm to 22 cm, 6 mm to 20 cm, 10 mm to 17 cm, 7.5 nm to 20 cm, 7.5 mm to 10 cm, 5 mm to 16 mm, 4 mm to 20 mm, and 8 mm to 12 cm. Any two values within the range of 3 mm to 25 cm therefore can be used to set the lower and upper boundaries of a range in accordance with the embodiments of the present disclosure.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

The inventive concepts of the present disclosure will be more readily understood by reference to the following examples and embodiments, which are included merely for purposes of illustration of certain aspects and embodiments thereof, and are not intended to be limitations of the disclosure in any way whatsoever. Those skilled in the art will promptly recognize appropriate variations of the apparatus, compositions, components, procedures and method shown below.

Figure 9:
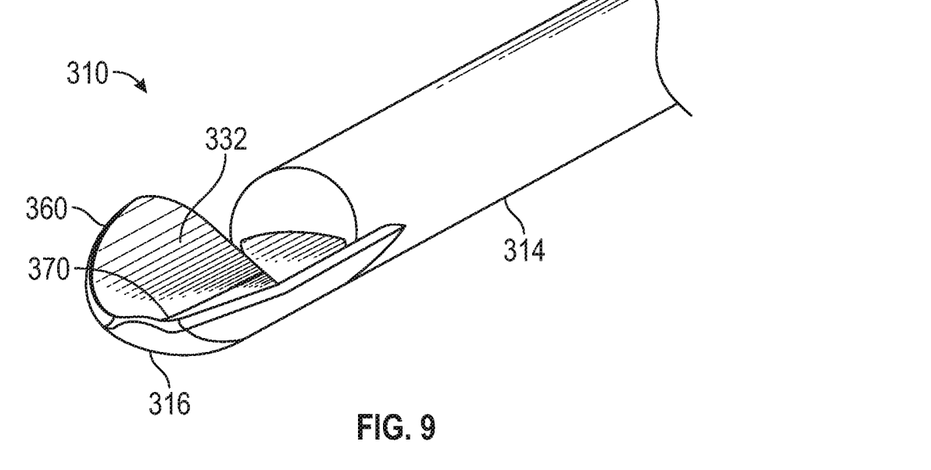
FIG. 9 is a perspective view of another embodiment of a surgical evacuation apparatus having a scoop shown in an expanded position.
Figure 10:
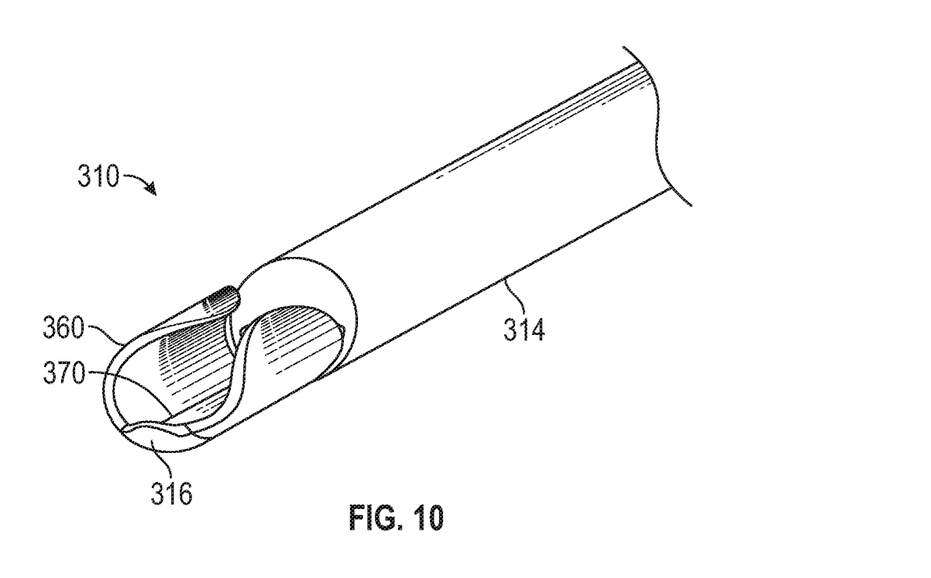
FIG. 10 is a perspective view of the surgical evacuation apparatus of FIG. 9 showing the scoop in a collapsed position.
Figure 11:
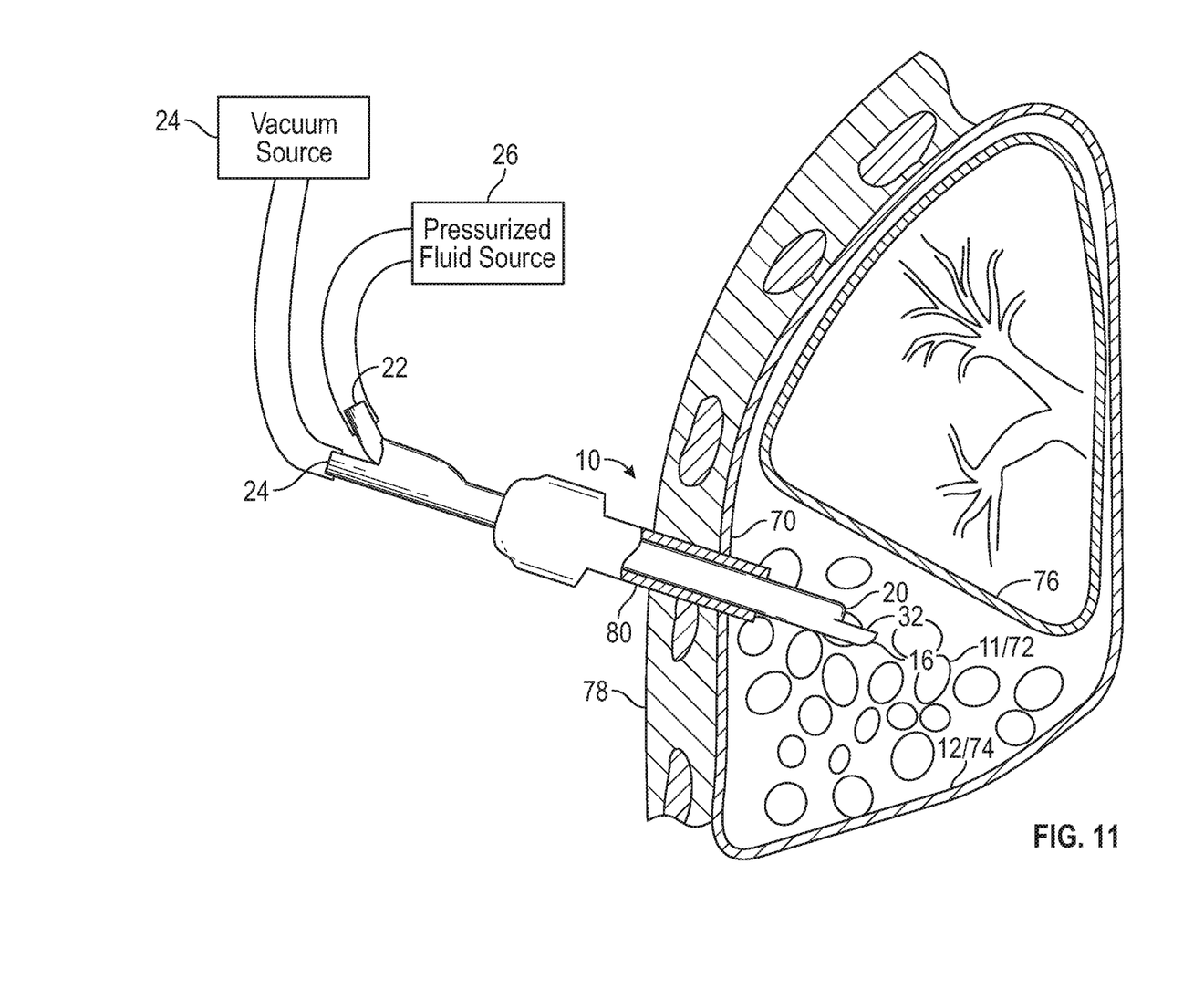
FIG. 11 is a diagrammatic view illustrating use of the surgical evacuation apparatus of FIG. 1 shown inserted into a thoracic cavity of a patient.

Referring now to FIGS. 1-11, a surgical evacuation apparatus 10 for evacuating a biological material, such as biological material 11 (FIGS. 6 and 11) from a body cavity, such as body cavity 12 (FIG. 11), is illustrated. The body cavity 12 illustrated in FIG. 11 is a thoracic cavity 70 filled with biological material in the form of pooled blood 72 in a pleural space 74, in which a lung 76 is shown partially collapsed, a condition referred to as hemothorax. A method of evacuating biological material may therefore include thorascopic removal of hemothorax. However, it should be appreciated that the surgical evacuation apparatuses described herein may be used in a variety of minimally invasive surgeries including, but not limited to, thorascopic removal of hemothorax, thorascopic removal of empyema, laparoscopic debridement of liver or liver abscess, and other instances of removal of deleterious materials from pleural, peritoneal, and abdominal cavities, knee or shoulder joint capsules, or other body cavities.

As noted above, systems such as the VERSAJET™ tangential hydrosurgery system have been used to deliver a liquid jet directly to a tissue surface of a subject for uses such as debridement of wounds. In this system a high pressure fluid jet running parallel to a tissue surface draws devitalized soft tissues into a cutting chamber for excision and evacuation. However, these devices can cause unintended damage to surrounding vital tissue, which is particularly undesirable for cases of removal of debris from delicate surgical sites. In the novel devices of the present disclosure, the fluid stream is oriented such that it does not directly contact intact living tissue of the subject.

Figure 1:
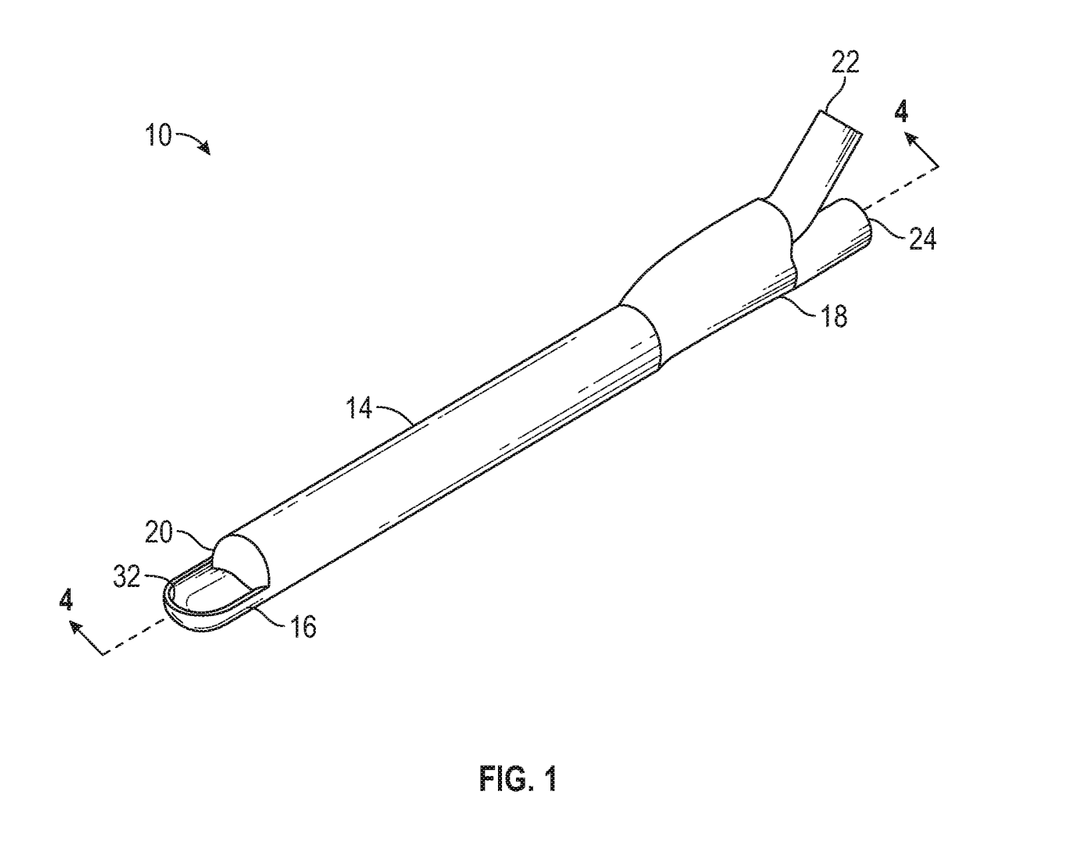
FIG. 1 is a perspective view of a surgical evacuation apparatus constructed in accordance with the inventive concepts disclosed herein.
Figures 2, 3:
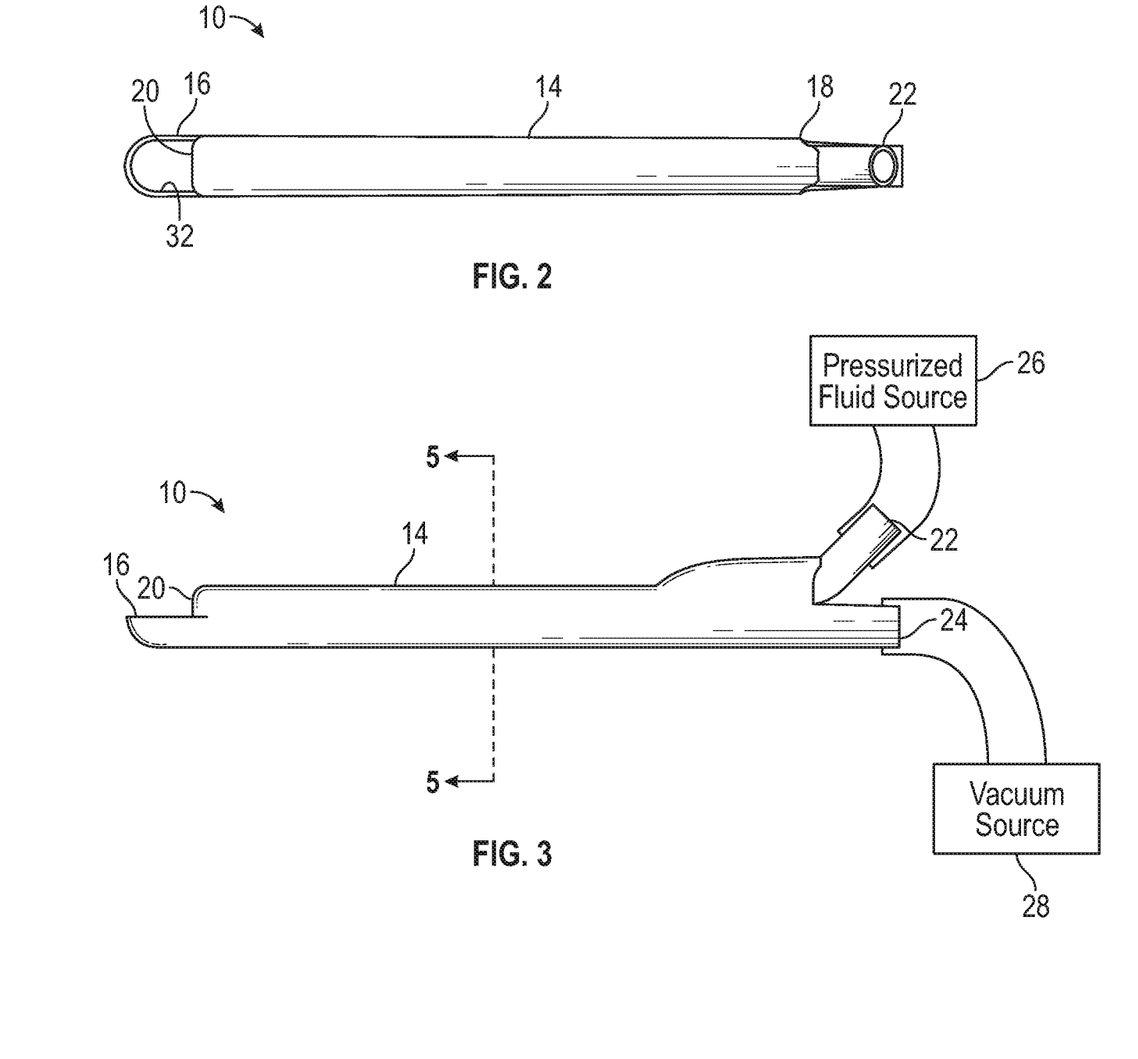
FIG. 2 is a top plan view of the surgical evacuation apparatus of FIG. 1.
FIG. 3 is a side elevational view of the surgical evacuation apparatus of FIG. 1 shown connected to a pressurized fluid source and a vacuum source.

As shown in FIGS. 1 and 2, the surgical evacuation apparatus 10 has a shaft 14 and a scoop 16 extending from the shaft 14. The shaft 14 includes a proximal end 18 and a distal end 20. The proximal end 18 has an inlet 22 for connecting to a pressurized fluid source 26 (FIG. 3) and an outlet 24 for connecting to a vacuum source 28 (FIG. 3). The scoop 16 extends from the distal end 20 of the shaft 14 and defines a material collecting cavity 32 where the biological material 11 is collected before it is evacuated from the body cavity 12 through the shaft 14.

Figure 4:
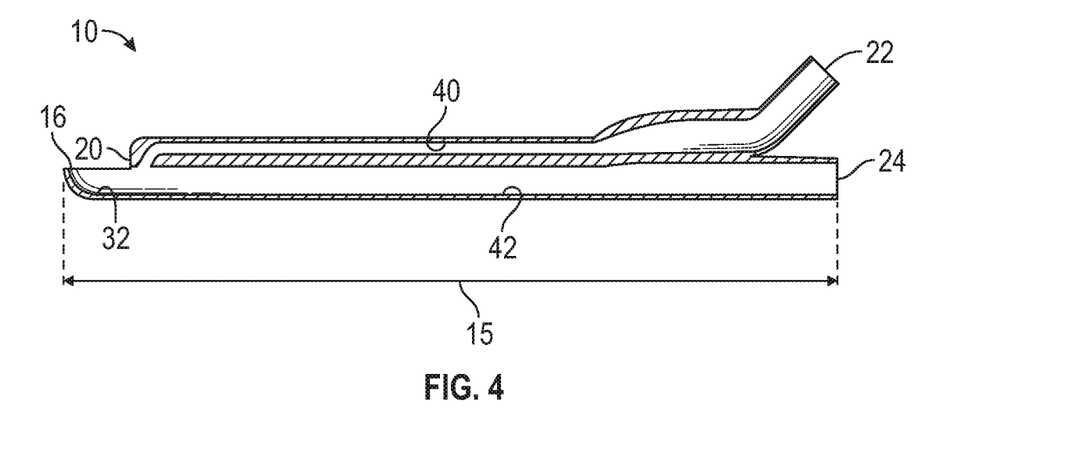
FIG. 4 is cross-sectional view taken along line 4-4 of FIG. 1.
Figure 5:
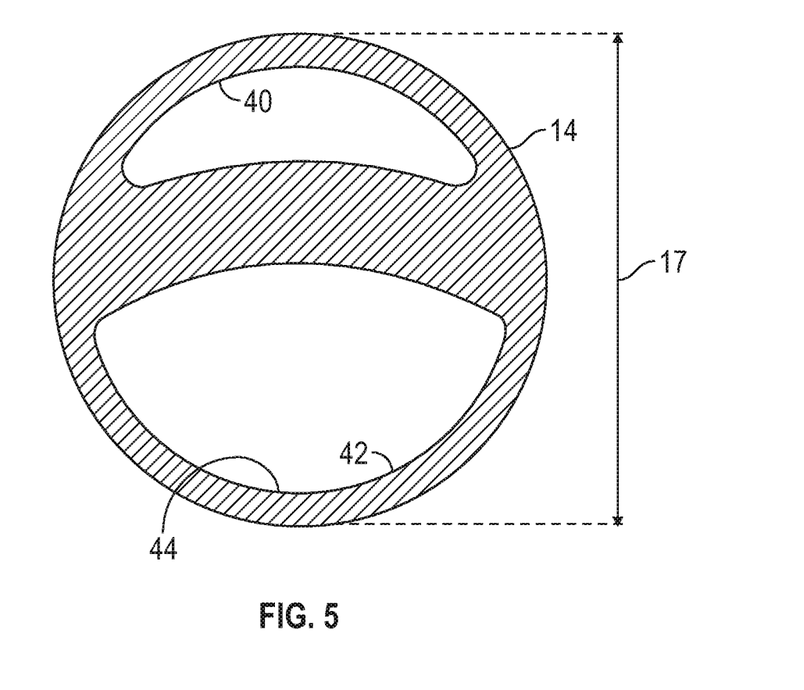
FIG. 5 is a cross-sectional view taken along line 5-5 of FIG. 3.

As shown in FIG. 4, the shaft 14 includes a supply channel 40 and an evacuation channel 42. The evacuation channel 42 extends through the shaft 14 from the distal end 20 to the outlet 24 such that the evacuation channel 42 is in open communication with the material collecting cavity 32. The supply channel 40 extends through the shaft 14 from the inlet 22 towards the distal end 20 and intersects with the evacuation channel 42 proximate the scoop 16. The shaft 14 has a length 15 and an outer diameter 17 (FIG. 5). The scoop 16 has a length 19 (FIG. 6).

The supply channel 40 and the evacuation channel 42 in the shaft 14 may be formed of a variety of shapes and sizes. In one embodiment shown in FIG. 5, the evacuation channel 42 is configured to have an arch shape in an upper portion thereof to increase volume and allow for enhanced movement of the biological material 11 through the evacuation channel 42. As shown in FIG. 5, the supply channel 40 may also be curved or arched to substantially correspond to the shape of the evacuation channel 42. In the embodiment in FIG. 5, the corners of the evacuation channel 42 and the supply channel 40 are rounded to increase overall strength and decrease the chances of the evacuation channel 42 and supply channel 40 becoming clogged.

Figure 6:
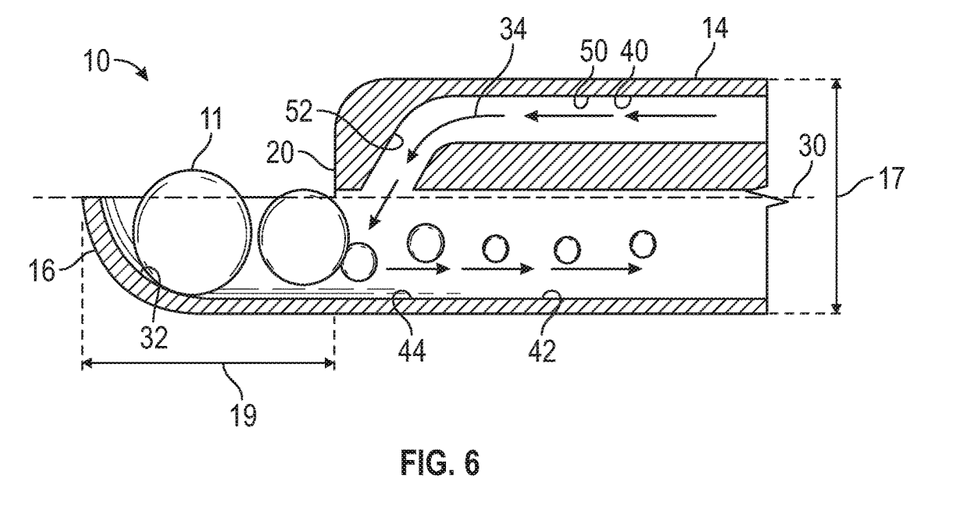

As illustrated in FIG. 6, the biological material 11 may be collected in the material collecting cavity 32 of the scoop 16 and may be drawn into the evacuation channel 42 when a vacuum is applied to the outlet 24. The biological material 11 may be broken up in the evacuation channel 42 by a fluid stream 34, passing into the evacuation channel 42 from the supply channel 40, and from the pressurized fluid source 26. The surgical evacuation apparatus 10 may therefore facilitate evacuation of the biological material 11.

The shaft 14 has a longitudinal axis 30. The outer diameter 17 of the shaft 14 may be in a range of about 5 mm to about 15 mm (for example, 5 mm, 6 mm, 7 mm, 8 mm, 9 mm, 10 mm, 11 mm, 12 mm, 13 mm, 14 mm, or 15 mm, or any fraction between said integer values). In one embodiment, the outer diameter 15 of the shaft 14 is in a range of about 10 mm to 12 mm. The outer diameter 15 of the shaft 14 may be sized to fit within an interior of an access port 80 such as shown in FIG. 11 and discussed in further detail below. In non-limiting embodiments, the length 15 of the shaft 14 may be in a range of about 20 cm to about 40 cm. In one embodiment, for example, the shaft 14 has a length 15 in a range of about 25 cm to 35 cm. In one embodiment, for example, the shaft 14 has a length 15 of about 30 cm. As shown in FIGS. 1 and 5, the shaft 14 has a cylindrical shape. However, it should be appreciated that the shaft 14 may be formed of a variety of shapes. The shaft 14 may be constructed of any desired material, such as stainless steel, surgical steel, titanium, metals, anodized aluminum, non-metals, polyether ether ketone (PEEK), polymers, resins, or combinations thereof, and may be constructed using any desired manufacturing technique, such as machining, casting, molding, or combinations thereof.

In certain embodiments, the material used to construct the shaft 14 provides the supply channel 40 with sufficient burst strength to enable it to conduct the fluid stream 34 through the supply channel 40 at a sufficiently high fluid pressure for the fluid stream 34 to break up the biological material 11 inside the evacuation channel 42. The burst strength of the supply channel 40 and the evacuation channel 42 may be selected to meet the highest contemplated pressure of the fluid stream 34 supplied for use in the specific surgical procedure to be performed. For example, the surgical evacuation apparatus 10 may operate at fluid pressure between about 1,000 psig and about 15,500 psig, depending on the intended material to be broken up. However, the fluid stream 34 should not exit the shaft 14 directly through the scoop 16. It is desired that the fluid of the fluid stream 34 be substantially contained within the supply channel 40 or the evacuation channel 42 unless is it being evacuated through the outlet 24. It should be appreciated that those having ordinary skill in the art will readily be able to select appropriate materials for forming the supply channel 40 and the evacuation channel 42 for particular surgical requirements.

The pressurized fluid source 26 may be any suitable pump capable of supplying the fluid pressures required for performing the desired surgical procedure. Those having ordinary skill in the art should appreciate that many types of high pressure pumps may be utilized for the present purpose, including, but not limited to, piston pumps and diaphragm pumps.

The vacuum source 28 may be any vacuum source well known in the surgical industry to provide suction to the surgical evacuation apparatus 10 in the manner described above and as is required for the desired surgical procedure. The vacuum should be sufficient to evacuate the tissue;

however, the vacuum should not be so strong so as to cause damage to any internal organs. The vacuum should also not cause a lung to expand in a way that may hinder a surgeon's view when the surgical evacuation apparatus 10 is used in a thoracic cavity. The surgical evacuation apparatus may operate at a vacuum level between about 50 mmHg and about 550 mmHg, depending on the vacuum level required to evacuate the biological material.

Examples of pressurized fluid sources and/or vacuum sources that may be used with the surgical evacuation apparatuses of the present disclosure include, but are not limited to, those described in U.S. Pat. Nos. 3,804,089, 3,955,579, 4,959,049, 5,295,980, 5,685,840, 6,960,182, 7,431,711, and 7,938,794, and in U.S. Patent Application Publication Nos. 20030125660, 20040234380, 20060264808, 20100094313, 20110150680, 20120078233, and 20150122119, each of which is incorporated by reference herein in its entirety.

The fluid stream 34 may comprise any fluid that can be maintained in a liquid state at the pressures and temperatures contemplated for performing surgical procedures. For applications in which the instruments are used to perform surgical procedures in a live patient, the fluid utilized should also be physiologically compatible. For example, in some embodiments, the fluid supplied may be a sterile surgical saline solution. In some embodiments, in order to improve the ability of the fluid stream 34 to break up the biological material, the fluid may contain solid abrasives, or the fluid may comprise a liquefied gas.

The supply channel 40 of the shaft 14 intersects the evacuation channel 42 in such, an orientation that the first impact of the fluid stream 34 is directed toward a portion of a lower surface 44 of the evacuation channel 42 proximate to the scoop 16, whereby the fluid stream 34 is inhibited from directly contacting a body tissue such as an epithelium that is not desired to be disturbed by the surgical procedure. For example, in the embodiment shown in FIGS. 4 and 6, the supply channel 40 has a first portion 50 and a second portion 52. The first portion 50 is parallel to the evacuation channel 42 and the second portion 52 extends toward the distal end 20 of the shaft 14 and is angled acutely relative to the longitudinal axis 30 of the shaft 14.

Figure 7:
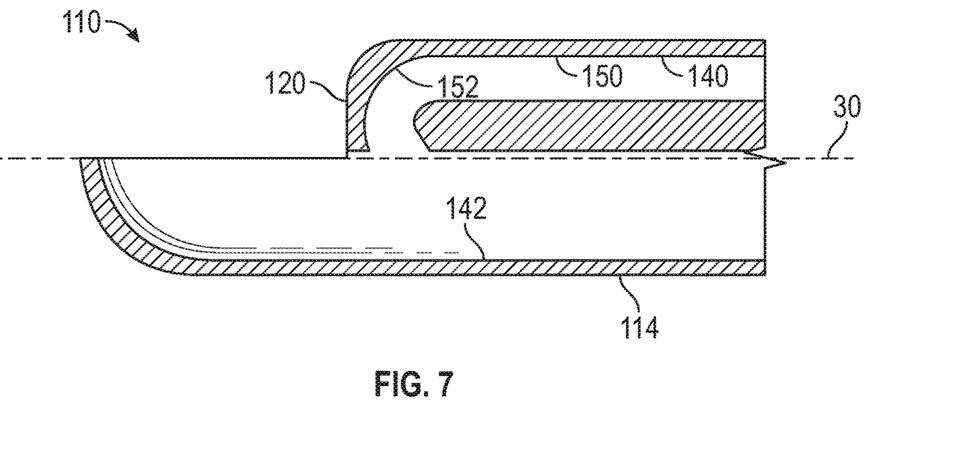
FIG. 7 is a cross-sectional view of another embodiment of a surgical evacuation apparatus.

FIG. 7 shows another embodiment of surgical evacuation apparatus, such as surgical evacuation apparatus 110. The surgical evacuation apparatus 110 has a shaft 114 having a distal end 120, a longitudinal axis 130, a supply channel 140 and an evacuation channel 142. The supply channel 142 has a first portion 150 and second portion 152. The second portion 152 of the supply channel 140 extends away from the distal end 120 of the shaft 114 and is angled obtusely relative to the longitudinal axis 130 of the shaft 114. The surgical evacuation apparatus 110 may be otherwise constructed substantially similar to surgical evacuation apparatus 110.

Figure 8:
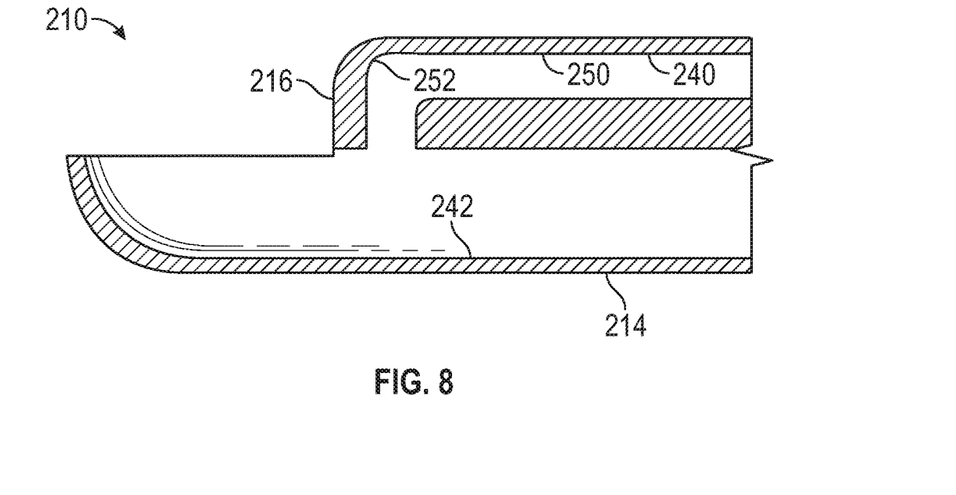
FIG. 8 is a cross-sectional view of another embodiment of a surgical evacuation apparatus.

FIG. 8 shows yet another embodiment of a surgical evacuation apparatus, such as surgical evacuation apparatus 210. The surgical evacuation apparatus 210 has a shaft 214 having a supply channel 240 and an evacuation channel 242. The supply channel 242 has a first portion 250 and second portion 252. The second portion 252 of the supply channel 240 is perpendicular to the evacuation channel 242. The surgical evacuation apparatus 210 may be otherwise constructed substantially similar to surgical evacuation apparatus 10.

The scoop 16 may have a variety of sizes suitable for collecting the bodily material 11. For example, the length 19 of the scoop 16 may be in a range of about 5 mm to about 30 mm. In the embodiment shown in FIG. 1, the scoop 16 has a width substantially equal to the outer diameter 17 of the shaft 14. In one embodiment, the scoop 16 extends coextensively from the shaft 14 and may also constructed of any desired material, such as stainless steel, surgical steel, titanium, metals, anodized aluminum, non-metals, polyether ether ketone (PEEK), polymers, resins, or combinations thereof, and may be constructed using any desired manufacturing technique, such as machining, casting, molding, or combinations thereof. However, it should be appreciated that the scoop 16 made may be formed of a separate construction and may be connected to the shaft 14.

FIGS. 9 and 10 show another embodiment of a scoop, such as scoop 316, extending from a shaft 314 of a surgical evacuation apparatus 310. Scoop 316 includes a pair of wings 360. The wings 360 are flexible so as to be movable between an expanded ("open") position (shown in FIG. 9) and a retracted ("closed") position (shown in FIG. 10). When the wings 360 are in the expanded position, the ability of the scoop 316 to collect the biological material 11 into a material collecting cavity, such as material collecting cavity 332, may be enhanced. The wings 360 are caused to fold into the retracted position as the shaft 314 is inserted into and removed from an opening in the body wall of the patient. In other words, the wings 360 may be guided through an opening when they are in the retracted position. Alternatively, when a port is used during the surgical procedure (as discussed below regarding FIG. 11), the wings 360 are caused to fold into the retracted position as the shaft 314 is inserted into and removed from the port. The scoop 316 may be constructed of any suitable flexible, biocompatible materials and may be constructed using any desired manufacturing technique, such as those listed above. For example, the scoop 316 may be constructed of a flexible silicone material.

In one non-limiting embodiment, the scoop 316 further includes a spine 370 extending from a distal end the shaft 314. The pair of wings 316 extends from the spine 370 and fold in a radial direction about the spine 370 when the wings 360 are in the retracted position. The spine 370 is formed of a different and more rigid material than the wings 360 for providing stiffness to the scoop 316 and may be formed of the same material as the shaft 314, such as, stainless steel, surgical steel, titanium, metals, anodized aluminum, non-metals, polyether ether ketone (PEEK), polymers, resins, or combinations thereof, or from any other suitable rigid material.

Referring now to FIG. 11, a method for evacuating the biological material 11 from the body cavity 12 is described. The body cavity illustrated in FIG. 11 is the thoracic cavity 70 filled with the biological material 11/blood tissue 72 in the pleural space 74, in which the lung 76 is shown partially collapsed, a condition referred to as hemothorax. The method of evacuating biological material may therefore include thorascopic removal of hemothorax. However, it should be appreciated that the surgical evacuation apparatuses 10, 110, 210, and 310, described herein, may be used in a variety of minimally invasive surgeries including, but not limited to, thorascopic removal of hemothorax, thorascopic removal of empyema, and laparoscopic debridement of liver or liver abscess.

To evacuate the biological material 11/blood tissue 72 from the body cavity 12 (or pleural space 74), a surgical evacuation apparatus, such as surgical evacuation apparatus 10, 110, 210, or 310 is first obtained. For purposes of clarity, a method of using surgical evacuation apparatus 10 is described; however, it should be appreciated that the method described herein may also include surgical evacuation apparatuses 110, 210, or 310.

After obtaining the surgical evacuation apparatus 10, the distal end 20 of the surgical evacuation apparatus 10 is inserted through an opening in a body wall 78 of the patient. In certain embodiments of the method of use, before the shaft 14 and scoop 16 of the surgical evacuation apparatus 10 are inserted into the opening of the body wall 78 of the patient, a rigid or semi-rigid port, such as port 80, is first inserted into the opening of the body wall 78 in order to create a channel or corridor through which the shaft 14 and scoop 16 may then be inserted, as shown in FIG. 11. Such ports are known in the art and any commercially available port commonly used for providing access to a surgical site through a body wall of a patient may be used. The surgical evacuation apparatus 10 is then advanced into the thoracic cavity 70 and into the pleural space 74. The pressurized fluid 34 from the pressurized fluid source 26 is applied to the inlet 22, and a vacuum from the vacuum source 28 is applied to the outlet 24. As noted above, when the surgical evacuation apparatus 310 of the embodiment of FIGS. 9 and 10 is used, the wings 360 of the scoop 316 move to a retracted position upon coming into contact with an open end of the port 80 and move into the interior of the port 80, and move to an expanded position when the scoop 316 emerges from the interior of the port 80.

Next, the biological material 11 is collected into the material collecting cavity 32 defined by the scoop 16 (or other scoop defined herein). After the biological material 11 has been collected in the material collecting cavity 32, the biological material 11 is drawn from the material collecting cavity 32 into the evacuation channel 42 by suction from the vacuum source 28. The biological material 11 is then broken up (macerated) within the evacuation channel 42 proximate the scoop 16 (e.g., see FIG. 6) by the force of the fluid stream 36. Finally, the broken up biological material 11 is drawn from the patient's body cavity 70 through the outlet 24. Therefore, the biological material 11 is able to be collected and evacuated without applying the fluid stream 34 directly to any tissue located inside a patient's body and without the use of multiple instruments.

Finally, the surgical evacuation apparatus 10 is removed from the patient's body. In the method using the port 80, the shaft 14 and the scoop 16 are removed from the port 80. In an embodiment wherein the scoop 316 includes a pair of wings, such as wings 360, the wings 360 move to the retracted position as they come into contact with a distal end of the port 80 and are drawn into the interior of the port 80. The port 80 is then removed, and the opening in the body wall 78 is then closed. The surgical evacuation apparatus 10, 110, 210, or 310 may be provided with the port 80 as a kit for ease of use and to further save time during the surgical procedure.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the devices, components and methods described herein, and in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. A surgical evacuation apparatus for evacuating a biological material, comprising:
   a shaft having a proximal end and a distal end, the proximal end having an inlet for connecting to a pressurized fluid source and an outlet for connecting to a vacuum source, and
   a scoop extending from the distal end of the shaft and defining a material collecting cavity; and
   wherein the shaft further comprises a supply channel and an evacuation channel, the evacuation channel starting at the distal end of the shaft and extending through the shaft from the distal end to the outlet in a way that the evacuation channel is in open communication with the material collecting cavity, and the supply channel extending through the shaft from the inlet towards the distal end and intersecting the evacuation channel at a location along the evacuation channel separate from an entirety of the material collecting cavity of the scoop such that the biological material collected in the material collecting cavity is drawn into the evacuation channel from the material collecting cavity when a vacuum is applied to the outlet and the biological material is broken up in the evacuation channel by a fluid stream passing into the evacuation channel from the supply channel to facilitate evacuation of the biological material.

2. The surgical evacuation apparatus of claim 1, wherein the scoop extends coextensively from the distal end of the shaft.

3. The surgical evacuation apparatus of claim 1, wherein the scoop comprises a pair of wings movable between an expanded position and a retracted position.

4. The surgical evacuation apparatus of claim 1, wherein the scoop comprises a pair of wings movable between an expanded position and a retracted position, the scoop having a width greater than an outer diameter of the shaft when the wings are in the expanded position, and wherein the scoop has a width substantially equal to the outer diameter of the shaft when the wings are in the retracted position.

5. The surgical evacuation apparatus of claim 1, wherein the shaft further has a longitudinal axis, and wherein the supply channel comprises a first portion and a second portion, the first portion being parallel to the evacuation channel and the second portion extending toward the distal end and being angled acutely relative to the longitudinal axis of the shaft.

6. The surgical evacuation apparatus of claim 1, wherein the shaft further has a longitudinal axis, and wherein the supply channel comprises a first portion and a second portion, the first portion being parallel to the evacuation channel and the second portion extending away from the distal end and being angled obtusely relative to the longitudinal axis of the shaft.

7. The surgical evacuation apparatus of claim 1, wherein the supply channel further comprises a first portion and a second portion, the first portion being parallel to the evacuation channel and the second portion being perpendicular to the evacuation channel.

8. The surgical evacuation apparatus of claim 1, wherein the shaft has an outer diameter in a range of about 5 mm to about 15 mm.

9. A surgical evacuation apparatus in combination with a pressurized fluid source and a vacuum source, the surgical evacuation apparatus comprising:
- a shaft having a proximal end and a distal end, the proximal end having an inlet connected to the pressurized fluid source and an outlet connected to the vacuum source, and
- a scoop extending from the distal end of the shaft and defining a material collecting cavity; and
- wherein the shaft further comprises a supply channel and an evacuation channel, the evacuation channel starting at the distal end of the shaft and extending through the shaft from the distal end to the outlet in a way that the evacuation channel is in open communication with the material collecting cavity, and the supply channel extending through the shaft from the inlet towards the distal end and intersecting the evacuation channel at a location along the evacuation channel separate from an entirety of the material collecting cavity of the scoop such that biological material collected in the material collecting cavity is drawn into the evacuation channel from the material collecting cavity by a vacuum from the vacuum source and is broken up in the evacuation channel by a fluid stream from the pressurized fluid source passing into the evacuation channel from the supply channel to facilitate evacuation of the biological material.

10. The surgical evacuation apparatus of claim 9, wherein the scoop extends coextensively from the distal end of the shaft.

11. The surgical evacuation apparatus of claim 9, wherein the scoop comprises a pair of wings movable between an expanded position and a retracted position.

12. The surgical evacuation apparatus of claim 9, wherein the scoop comprises a pair of wings movable between an expanded position and a retracted position, the scoop having a width greater than an outer diameter of the shaft when the wings are in the expanded position, and wherein the scoop has a width substantially equal to the outer diameter of the shaft when the wings are in the retracted position.

13. The surgical evacuation apparatus of claim 9, wherein the shaft has a longitudinal axis, and wherein the supply channel comprises a first portion and a second portion, the first portion being parallel to the evacuation channel and the second portion extending toward the distal end and being angled acutely relative to the longitudinal axis of the shaft.

14. The surgical evacuation apparatus of claim 9, wherein the shaft has a longitudinal axis, and wherein the supply channel comprises a first portion and a second portion, the first portion being parallel to the evacuation channel and the second portion extending away from the distal end and being angled obtusely relative to the longitudinal axis of the shaft.

15. The surgical evacuation apparatus of claim 9, wherein the supply channel comprises a first portion and a second portion, the first portion being parallel to the evacuation channel and the second portion being perpendicular to the evacuation channel.

16. The surgical evacuation apparatus of claim 9, wherein the shaft has an outer diameter in a range of about 5 mm to about 15 mm.

17. A method for evacuating biological material from a body cavity of a patient, the method comprising:
- obtaining a surgical evacuation apparatus comprising (1) a scoop which defines a material collecting cavity, and (2) a shaft having a proximal end and a distal end, the scoop extending from the distal end, and the proximal end having an inlet and an outlet, the shaft comprising a supply channel extending from the inlet toward the distal end and an evacuation channel starting at the distal end of the shaft and extending from the distal end to the outlet, wherein the supply channel intersects the evacuation channel at a location along the evacuation channel separate from an entirety of the material collecting cavity of the scoop and is in fluid communication with the evacuation channel;
- connecting the inlet to a pressurized fluid source;
- connecting the outlet to a vacuum source;
- inserting the surgical evacuation apparatus through an opening in a body wall of the patient;
- advancing the surgical evacuation apparatus into the body cavity of the patient;
- supplying a pressurized fluid from the pressurized fluid source to the inlet;
- applying a vacuum from the vacuum source to the outlet;
- collecting the biological material into the material collecting cavity of the scoop;
- drawing the biological material from the material collecting cavity into the evacuation channel with the vacuum from the vacuum source;
- breaking up the biological material in the evacuation channel by passing a fluid stream from the supply channel into the evacuation channel; and
- drawing the broken up biological material from the body cavity through the outlet.

18. The method of claim 17, wherein the scoop extends coextensively from the distal end of the shaft.

19. The method of claim 17, wherein the scoop comprises a pair of wings movable between an expanded position and a retracted position.

20. The method of claim 17, wherein the scoop comprises a pair of wings movable between an expanded position and a retracted position, the scoop having a width greater than an outer diameter of the shaft when the wings are in the expanded position, and wherein the scoop has a width substantially equal to the outer diameter of the shaft when the wings are in the retracted position.

\* \* \* \* \*